United States Patent [19]

Mehta et al.

[11] Patent Number: 4,593,108

[45] **Date of Patent: * Jun. 3, 1986**

[54] 1-PHENYL-5-MERCAPTO TETRAZOLES

[75] Inventors: Avinash C. Mehta, Belmont; George H. Nawn, Westwood; Lloyd D. Taylor, Lexington, all of Mass.

[73] Assignee: Polaroid Corporation, Cambridge, Mass.

[ * ] Notice: The portion of the term of this patent subsequent to Apr. 10, 2001 has been disclaimed.

[21] Appl. No.: 387,449

[22] Filed: Jun. 11, 1982

Related U.S. Application Data

[62] Division of Ser. No. 222,543, Jan. 5, 1981, Pat. No. 4,355,092.

[51] Int. Cl.[4] ............................................ C07D 257/04

[52] U.S. Cl. ..................................................... 548/251

[58] Field of Search ................................ 548/252, 251

[56] References Cited

U.S. PATENT DOCUMENTS

| | | | |
|---|---|---|---|
| 2,725,290 | 11/1955 | Smith | 95/2 |
| 3,260,597 | 7/1966 | Weyerts et al. | 96/3 |
| 3,265,498 | 8/1966 | Rogers et al. | 96/3 |
| 3,295,976 | 11/1967 | Abbott et al. | 96/55 |
| 3,376,310 | 9/1964 | Abbott et al. | 548/251 |
| 3,377,166 | 4/1968 | Weyerts et al. | 96/29 |
| 3,615,438 | 10/1971 | Land | 96/29 |
| 3,632,345 | 11/1972 | Marx | 548/251 X |
| 3,698,898 | 10/1972 | Grasshoff et al. | 96/3 |
| 4,009,029 | 2/1977 | Hammond et al. | 96/3 |
| 4,063,950 | 12/1977 | Fujiwhara et al. | 548/253 X |
| 4,088,491 | 5/1978 | Odenwalder et al. | 96/55 |
| 4,131,467 | 2/1979 | Bigelow | 96/66.3 |
| 4,190,666 | 2/1980 | Cherkofsky et al. | 424/274 |
| 4,442,290 | 4/1984 | Bartels-Keith et al. | 548/251 |

FOREIGN PATENT DOCUMENTS

| | | | |
|---|---|---|---|
| 2427183 | 6/1974 | Fed. Rep. of Germany . | |
| 57-118245 | 7/1982 | Japan | 548/251 |
| 1487461 | 9/1977 | United Kingdom . | |
| 1533895 | 11/1978 | United Kingdom . | |
| P55858 | 7/1982 | United Kingdom | 548/251 |

*Primary Examiner*—Richard L. Raymond
*Assistant Examiner*—D. B. Springer
*Attorney, Agent, or Firm*—Gaetano D. Maccarone

[57] ABSTRACT

There are disclosed novel compounds which are represented by the formula

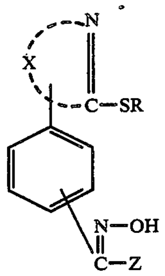

wherein X represents the nonmetallic atoms necessary to form a nucleus which completes a 5- or 6-membered heterocyclic moiety, R is H, an alkali metal or a group which is cleavable in aqueous alkaline medium and Z is H, alkyl having from 1 to 10 carbon atoms, aralkyl such as benzyl or phenethyl, phenyl or substituted phenyl. The compounds are useful in photographic applications.

8 Claims, 2 Drawing Figures

1-PHENYL-5-MERCAPTO TETRAZOLES

CROSS-REFERENCE TO RELATED APPLICATION

This application is a division of prior copending application Ser. No. 222,543, filed Jan. 5, 1981 now U.S. Pat. No. 4,355,092, issued Oct. 19, 1982.

BACKGROUND OF THE INVENTION

The application relates generally to novel compounds and, more specifically, to compounds which are useful in photography.

Diffusion transfer photographic systems wherein images are formed in color by the use of image dye-providing materials such as dye developers are well known in the art. Generally, multicolor transfer images are formed by processing an exposed multicolor photosensitive silver halide element with an aqueous alkaline processing composition distributed between two sheet-like elements, one of these elements including an image receiving layer. The processing composition is so applied and confined within and between the two sheet-like elements as not to contact or wet outer surfaces of the two superposed elements, thus providing a film unit whose external surfaces are dry. The processing composition preferably is distributed in viscous form from a pressure rupturable container.

It is known in the art to carry out development in the presence of development restrainers whereby development of exposed silver halide is continued for a period of time sufficient to form an imagewise distribution of diffusible unoxidized dye developers in undeveloped areas of the silver halide emulsion layer(s) with the unoxidized dye developers being transferred by diffusion to a superposed image receiving element and, after the predetermined development period, restraining further development of silver halide by means of the development restrainer. See, for example, U.S. Pat. No. 3,265,498. Various development restrainers which are useful for such purposes are known including mercaptoazoles such as 1-phenyl-5-mercaptotetrazole. However, the use of such development restrainers is subject to certain limitations. For example, U.S. Pat. No. 3,260,597 discloses that mercaptoazole development restrainers or "arrestors", such as 1-phenyl-5-mercaptotetrazole, can not be used in the aqueous alkaline processing composition in any appreciable amount because development of exposed silver halide will be stopped prematurely particularly in the outer blue and green sensitive emulsion layers of a multicolor system.

It is also known in the art to use blocked development restrainers which are designed to provide a timed release of a development restrainer during the development process. See, for example, U.S. Pat. No. 3,698,898 which discloses the use of quinone- or naphthoquinone-methide precursors which release a photographic reagent such as 1-phenyl-5-mercaptotetrazole in the presence of alkali; U.S. Pat. No. 4,009,029 which discloses a class of cyanoethyl-containing blocked development restrainers; German Offenlegungsschrift No. 2,427,183 which discloses various blocked development restrainers, and U.S. Pat. Nos. 3,260,597 and 3,265,498, referred to above, which disclose hydrolyzable blocked restrainers.

The present application relates to novel phenylmercaptoazole compounds which are useful in photographic applications.

SUMMARY OF THE INVENTION

It is therefore the object of this invention to provide novel phenylmercaptoazole compounds.

It is another object to provide compounds which are useful in photographic applications.

It is a further object to provide compounds which include a blocking group designed to provide a timed release of the phenylmercaptoazole compounds during photographic processes.

Still another object is to provide photographic products and processes utilizing the phenylmercaptoazole compounds.

Yet another object is to provide diffusion transfer products and processes utilizing the phenylmercaptoazole compounds.

BRIEF SUMMARY OF THE INVENTION

These and other objects and advantages are accomplished in accordance with the invention by providing novel compounds which are represented by the formula

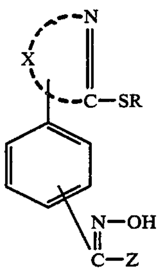

FORMULA A wherein X represents the nonmetallic atoms necessary to form a nucleus which completes a 5- or 6-membered heterocylic moiety including substituted rings and fused rings, R is H, an alkali metal or a group which is cleavable in an aqueous alkaline medium and Z is H, alkyl having from 1 to 10 carbon atoms, aralkyl such as benzyl or phenethyl, phenyl or phenyl substituted with substituents such as halogen, alkoxy or alkyl.

The novel compounds of the invention may have the substituted phenyl moiety attached to either a nitrogen atom or a carbon atom of the azole moiety. Accordingly, the compounds may be represented by either of the following formulas which are both within generic Formula A.

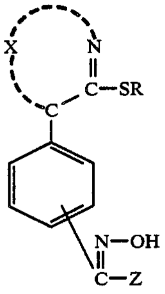

FORMULA B

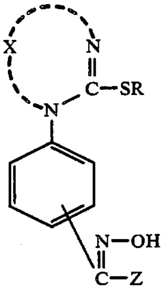

FORMULA C

The heterocyclic moieties formed by X preferably include those wherein the heterocyclic atoms (i.e., atoms other than carbon) are members of a single heterocyclic ring as contrasted with compounds containing fused or condensed heterocyclic rings in which the heterocyclic atoms are members of more than one heterocyclic ring. The compounds include monoazoles such as benzoxazoles, benzothiazoles and the like; diazoles such as benzimidazoles and the like; triazoles such as 1,2,4-triazoles and the like; tetrazoles and pyrimidines. In a preferred embodiment the compounds include a tetrazole nucleus.

As stated previously, R is either hydrogen, an alkali metal or a blocking group which is designed to cleave in an aqueous alkaline medium to provide timely release of the desired phenylmercaptoazole compound. Where R is a blocking group it may be any suitable blocking group such as, for example, those which cleave by hydrolysis; those which cleave by quinone methide elimination (e.g.

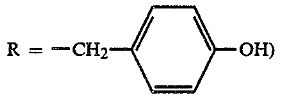

such as is disclosed in U.S. Pat. No. 3,698,898; those which cleave by hydrolysis followed by quinone methide elimination (e.g., R is

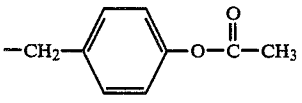

and those which cleave by β-elimination (e.g., R is $—CH_2—CH_2—CN$,

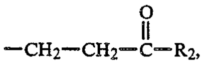, 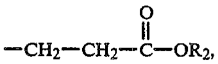, where $R_2$ is alkyl and

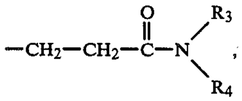, where $R_3$ and $R_4$ are H or alkyl. Typical suitable blocking groups include, for example,

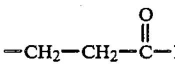, 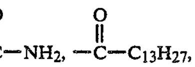,

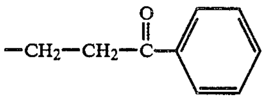,

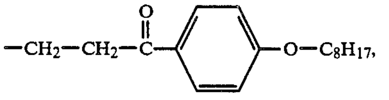,

-continued

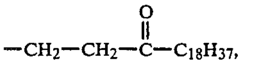,

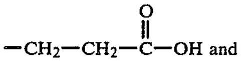 and 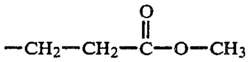

and succinimido groups which are substituted on the nitrogen atom with alkyl or aryl such as are described in U.S. Pat. No. 3,888,677.

In one embodiment of the invention R is $—CH_2—CH_2SO_2R_5$ where $R_5$ is alkyl, aryl or substituted aryl. Novel phenylmercaptoazole compounds having this sulfone blocking group and their use in photographic applications are disclosed and claimed generically in patent application of James R. Bartels-Keith and Alan L. Borror, Ser. No. 222,504, filed on even date herewith, abandoned.

The blocked compounds of the invention provide a timed release of a photographically useful material in the alkaline environment typically encountered in the processing of photographic elements and particularly where the alkaline medium has a pH in the range of from about 12 to about 14. The rate of release is dependent upon the hydroxyl ion concentration and therefore the rate of release increases as the pH increases. Upon cleavage of the molecule the heterocyclic ring taken together with the sulfur atom provides a photographically useful material. The cleavage reaction occurs according to the following sequence:

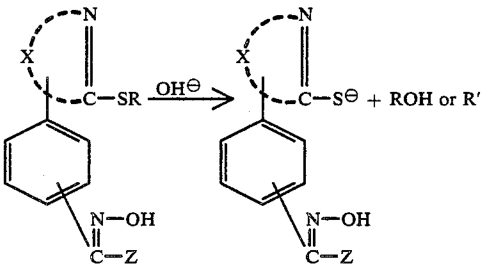

where R′ is R minus a proton.

The rate of release of the substituted phenylmercaptoazole moiety is also temperature dependent, that is, more is released as the temperature at which processing of the film unit is effect rises. Thus, more of the substituted phenylmercaptoazole moiety is made available at elevated temperatures, i.e., above room temperature, when more is typically desired, less is released at room temperature and even less below room temperature when lesser amounts are needed. Thus, the blocked compounds according to the invention provide more uniform sensitometry for the film units of the invention over a wide temperature range of processing. In other words, the sensitometry of the film units which include such blocked compounds according to the invention is less temperature dependent than would otherwise be the case.

The compounds of the invention are useful in photographic applications. In a preferred embodiment the compounds are utilized in diffusion transfer photographic products and processes to modify and/or control the sensitometry, particularly where processing is carried out at elevated temperatures, e.g., 95° F. Such modification and/or control of the sensitometry can provide desirable results including a speed increase for one or more of the individual colors in a multicolor diffusion transfer photographic system and/or an increase in the $D_{max}$ of one or more of the individual colors due to control of fog development, as will be illustrated in detail below herein.

BRIEF DESCRIPTION OF THE DRAWINGS

For a better understanding of the invention as well as other objects and further features thereof, reference is made to the following detailed description of various preferred embodiments thereof taken in conjunction with the accompanying drawings wherein.

DESCRIPTION OF THE PREFERRED EMBODIMENTS

Figure 1:
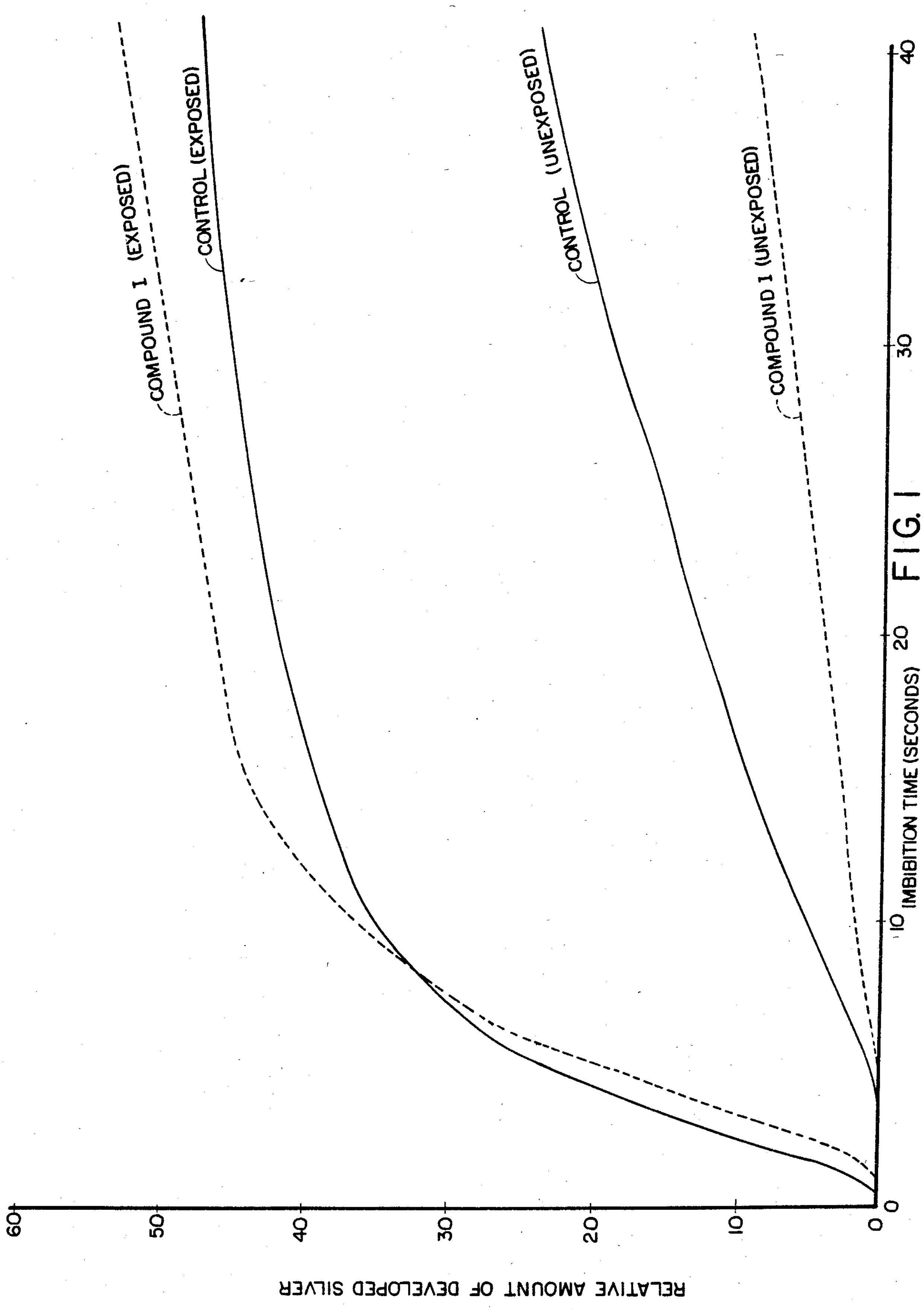
FIG. 1 is a graphical illustration of the relative amount of silver developed with respect to time in exposed and unexposed areas for a control film unit and a film unit including a compound of the invention, both processed at room temperature.

The compounds of the invention may be prepared by reactions which are known to those skilled in the art. For example, 2-mercaptoimidazoles can be prepared by the reactions disclosed in The Chemistry of Heterocyclic Compounds Vol. 6: Imidazole and Its Derivatives, Part I, Hofmann, Interscience Publishers, Inc., New York, 1953, pages 77-85; mercaptothiazoles and mercaptobenzothiazoles can be prepared according to the methods disclosed in The Chemistry of Heterocyclic Compounds, Vol. 34: Thiazole and Its Derivatives, Part I, Metzger, John Wiley and Sons, 1979, pages 260-269; Part 2, pages 370-377; benzoxazolethiones can be prepared according to the methods disclosed in Heterocyclic Compounds, Vol. 5, Elderfield, John Wiley and Sons, 1957, pages 439-444; 5-mercapto-1,3,4-oxadiazoles can be prepared according to the methods disclosed in Heterocyclic Compounds, Vol. 7, Elderfield, John Wiley and Sons, 1961, page 352; mercapto-1,3,4-thiadiazoles, ibid, pages 587-612; and tetrazoles by the techniques disclosed in Heterocyclic Compounds, Vol. 8, Elderfield, John Wiley and Sons, 1967, pages 1-107. Mercapto-1,2,4-triazoles can be prepared by known literature techniques as described, for example, in Jour. Chem. Soc., E. Hoggarth, 1163 (1949). Typically, the appropriate mercaptoazole oxime precursors are prepared with a

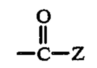

substituent on the phenyl ring (where Z is as previously defined) and subsequent oximation is easily achieved by reaction with hydroxylamine.

Particularly preferred compounds according to the invention are represented by the formulas:

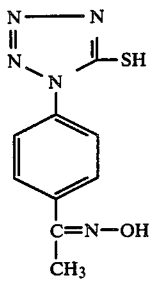

(I)

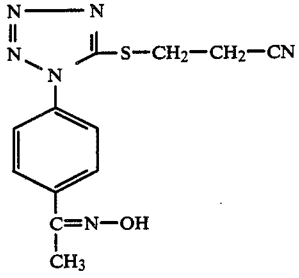

(II)

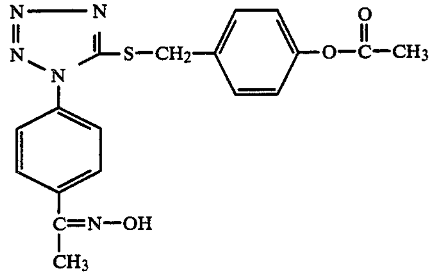

(III)

The phenylmercaptoazole compounds of the invention may be present in the photographic elements of the invention in any appropriate location and in any amount which is required to accomplish their intended purpose. The amount necessary in any particular instance is dependent upon a number of factors such as, for example, the specific compound, the type of photographic element, the location of the compound in the photographic element and the result desired. Routine scoping tests may be used to ascertain the concentration appropriate for any given film unit and location. In a preferred embodiment, the compounds are utilized in the diffusion transfer photographic products and processes disclosed and claimed in applicants' patent application Ser. No. 222,502 filed on even date herewith now U.S. Pat. No. 4,390,613. In such photographic film units, the compounds may be incorporated in the processing composition, the photosensitive element or the image receiving element or combination thereof. In a preferred embodiment the compounds of this invention are incorporated in more than one location in the diffusion transfer film unit. For example, part of the total quantity of the compound can be incorporated in the processing composition and the remainder in the photosensitive element. Thus, during the initial stages of development, the quantity available can be appropriate to provide a speed increase for one or more silver halide emulsions without providing any premature development restraint and the additional quantity dissolved during processing could give a total concentration desired to prevent further development. This embodiment is particularly useful where R is H or an alkali metal for the compound incorporated in the processing composition and R is a cleavable group for the compound incorporated in the photosensitive element.

As indicated previously, the compounds may be incorporated in film units in any useful amount. When utilized in diffusion transfer film units and incorporated in the processing composition it is preferred that they be present in an amount of from about 0.02 to about 0.07% by weight. It has been observed through experimentation that too great an amount of the compounds can lead to reduced control of one or more of the image dye-providing materials which results in high $D_{min}$ values in the photographic reproduction or can lead to a loss in Dmax for one or more colors.

The phenylmercaptoazole compounds may be used in association with any silver halide emulsion. It is preferred to use these compounds in a diffusion transfer photographic system which includes a negative working silver halide emulsion, i.e., one which develops in the areas of exposure. Further, these compounds may be used in association with any image dye-providing materials. In diffusion transfer photographic systems the image dye-providing materials which can be utilized generally may be characterized as either (1) initially soluble or diffusible in the processing composition but which are selectively rendered nondiffusible imagewise as a function of development; or (2) initially insoluble or nondiffusible in the processing composition but which selectively provide a diffusible product imagewise as a function of development. The image dye-providing materials may be complete dyes or dye intermediates, e.g., color couplers. The requisite differential in mobility or solubility may be obtained, for example, by a chemical reaction such as a redox reaction, a coupling reaction or a cleavage reaction. In a particularly preferred embodiment of the invention the image dye-providing materials are dye developers which are initially diffusible materials. The dye developers contain, in the same molecule, both the chromophoric system of a dye and a silver halide developing function as is described in U.S. Pat. No. 2,983,606. Other image dye-providing materials which may be used include, for example, initially diffusible coupling dyes such as are useful in the diffusion transfer process described in U.S. Pat. No. 3,087,817 and which are rendered nondiffusible by coupling with the oxidation product of a color developer; initially nondiffusible dyes which release a diffusible dye following oxidation, sometimes referred to as "redox dye releaser" dyes, such as described in U.S. Pat. Nos. 3,725,062 and 4,076,529; initially non-diffusible image dye-providing materials which release a diffusible dye following oxidation and intramolecular ring closure as are described in U.S. Pat. No. 3,433,939 or undergo silver assisted cleavage to release a diffusible dye in accordance with the disclosure of U.S. Pat. No. 3,719,489; and initially non-diffusible image dye-providing materials which release a diffusible dye following coupling with an oxidized color developer as described in U.S. Pat. No. 3,227,550.

The compounds may be incorporated into the photographic elements by any suitable technique. In embodiments where the compounds are incorporated in a layer within the film unit they are typically coated from a water or oil dispersion and the layer typically includes a binder material such as gelatin or the like.

The diffusion transfer film units in which the compounds may be utilized include those wherein the image-receiving element is designed to be separated from the photosensitive element after processing and integral positive-negative diffusion transfer film units which are retained intact after processing. In a preferred embodiment the diffusion transfer film units of the invention utilize initially diffusible dye developers as the image dye-providing materials. As described in U.S. Pat. No. 2,983,606, a photosensitive element containing a dye developer and a silver halide emulsion is photoexposed and a processing composition applied thereto, for example, by immersion, coating, spraying, flowing, etc., in the dark. The exposed photosensitive element is superposed prior to, during, or after the processing composition is applied, on a sheet-like support element which may be utilized as an image-receiving element. In a preferred embodiment, the processing composition is applied to the exposed photosensitive element in a substantially uniform layer as the photosensitive element is brought into superposed relationship with the image-receiving layer. The processing composition, positioned intermediate the photosensitive element and the image-receiving layer, permeates the emulsion to initiate development of the latent image contained therein. The dye developer is immobilized or precipitated in exposed areas as a consequence of the development of the latent image. This immobilization is apparently, at least in part, due to a change in the solubility characteristics of the dye developer upon oxidation and especially as regards its solubility in alkaline solutions. It may also be due in part to a tanning effect on the emulsion by oxidized developing agent, and in part to a localized exhaustion of alkali as a result of development. In unexposed and partially exposed areas of the emulsion, the dye developer is unreacted and diffusible and thus provides an imagewise distribution of unoxidized dye developer, diffusible in the processing composition, as a function of the point-to-point degree of exposure of the silver halide emulsion. At least part of this imagewise distribution of unoxidized dye developer is transferred, by imbibition, to a superposed image-receiving layer or element, said transfer substantially excluding oxidized dye developer. The image-receiving layer recieves a depthwise diffusion, from the developed emulsion, of unoxidized dye developer without appreciably disturbing the imagewise distribution thereof to provide a reversed or positive color image of the developed image. The image-receiving element may contain agents adapted to mordant or otherwise fix the diffused, unoxidized dye developer. In a preferred embodiment of said U.S. Pat. No. 2,983,606 and in certain commercial applications thereof, the desired positive image is revealed by separating the image-receiving layer from the photosensitive element at the end of a suitable imbibition period. Alternatively, as also disclosed in said U.S. Pat. No. 2,983,606, the image-receiving layer need not be separated from its superposed contact with the photosensitive element, subsequent to transfer image formation, if the support for the image-receiving layer, as well as any other layers intermediate said support and image-receiving layer, is transparent and a processing composition containing a substance, e.g., a white pigment, effective to mask the developed silver halide emulsion or emulsions is applied between the image-receiving layer and said silver halide emulsion or emulsions.

Dye developers, as noted in said U.S. Pat. No. 2,983,606, are compounds which contain, in the same molecule, both the chromophoric system of a dye and also a silver halide developing function. By "a silver halide developing function" is meant a grouping adapted to develop exposed silver halide. A preferred silver halide development function is a hydroquinonyl group. In general, the development function includes a benzonoid developing function, that is, an aromatic developing group which forms quinonoid or quinone substances when oxidized.

Multicolor images may be obtained using dye developers in diffusion transfer processes by several techniques. One such technique contemplates obtaining multicolor transfer images utilizing dye developers by employment of an integral multilayer photosensitive element, such as is disclosed in the aforementioned U.S. Pat. No. 2,983,606 and in U.S. Pat. No. 3,345,163, wherein at least two selectively sensitized photosensitive strata, superposed on a single support, are processed, simultaneously and without separation, with a single common image-receiving layer. A suitable arrangement of this type comprises a support carrying a red-sensitive silver halide emulsion stratum, a green-sensitive silver halide emulsion stratum and a blue-sensitive silver halide emulsion stratum, said emulsions having associated therewith, respectively, for example, a cyan dye developer, a magenta dye developer and a yellow dye developer. The dye developer may be utilized in the silver halide emulsion stratum, for example in the form of particles, or it may be disposed in a stratum behind the appropriate silver halide emulsion strata. Each set of silver halide emulsion and associated dye developer strata may be separated from other sets by suitable interlayers, for example, by a layer or stratum of gelatin or polyvinyl alcohol. In certain instances, it may be desirable to incorporate a yellow filter in front of the green-sensitive emulsion and such yellow filter may be incorporated in an interlayer. However, where desirable, a yellow dye developer of the appropriate spectral characteristics and present in a state capable of functioning as a yellow filter may be so employed and a separate yellow filter omitted.

Particularly useful products for obtaining multicolor dye developer images are disclosed in U.S. Pat. No. 3,415,644. This patent discloses photographic products wherein a photosensitive element and an image-receiving element are maintained in fixed relationship prior to exposure, and this relationship is maintained as a laminate after processing and image formation. In these products, the final image is viewed through a transparent (support) element against a light-reflecting, i.e., white background. Photoexposure is made through said transparent element and application of the processing composition provides a layer of light-reflecting material to provide a white background. The light-reflecting material (referred to in said patent as an "opacifying agent") is preferably titanium dioxide, and it also performs an opacifying function, i.e., it is effective to mask the developed silver halide emulsions so that the tranfer image may be viewed without interference therefrom, and it also acts to protect the photoexposed silver halide emulsions from post-exposure fogging by light passing through said transparent layer if the photoexposed film unit is removed from the camera before image-formation is completed.

U.S. Pat. No. 3,647,437 is concerned with improvements in products and processes disclosed in said U.S. Pat. No. 3,415,644, and discloses the provision of light-absorbing materials to permit such processes to be performed, outside of the camera in which photoexposure is effected, under much more intense ambient light conditions. A light-absorbing material or reagent, preferably a pH-sensitive phthalein dye, is provided so positioned and/or constituted as not to interfere with photoexposure but so positioned between the photoexposed silver halide emulsions and the transparent support during processing after photoexposure as to absorb light which otherwise might fog the photoexposed emulsions. Furthermore, the light-absorbing material is so positioned and/or constituted after processing as not to interfere with viewing the desired image shortly after said image has been formed. In the preferred embodiments, the light-absorbing material, also sometimes referred to as an optical filter agent, is initially contained in the processing composition together with a light-reflecting material, e.g., titanium dioxide. The concentration of the light-absorbing dye is selected to provide the light transmission opacity required to perform the particular process under the selected light conditions.

In a particularly useful embodiment, the light-absorbing dye is highly colored at the pH of the processing composition, e.g., 13–14, but is substantially non-absorbing of visible light at a lower pH, e.g., less than 10–12. This pH reduction may be effected by an acid-reacting reagent appropriately positioned in the film unit, e.g., in a layer between the transparent support and the image-receiving layer.

The dye developers are preferably selected for their ability to provide colors that are useful in carrying out subtractive color photography, that is, the previously mentioned cyan, magenta and yellow. The dye developers employed may be incorporated in the respective silver halide emulsion or, in the preferred embodiment, in a separate layer behind the respective silver halide emulsion, and such a layer of dye developer may be applied by use of a coating solution containing the respective dye developer distributed, in a concentration calculated to give the desired coverage of dye developer per unit area, in a film-forming natural, or synthetic, polymer, for example, gelatin, polyvinyl alcohol, and the like, adapted to be permeated by the processing composition.

Other diffusion transfer products and processes according to the invention are the types described in U.S. Pat. Nos. 3,573,043 and 3,594,165. For convenience, the entire disclosure of each of the six patents referred to immediately above is hereby incorporated by reference herein.

A particularly useful film unit according to the invention is one wherein the photosensitive element includes a light reflecting layer between the silver halide layer and the image dye-providing material layer (as described in Canadian Pat. No. 668,592), the substrate of the photosensitive element carries the polymeric acid neutralizing layer which in turn carries the timing layer (as described in U.S. Pat. No. 3,573,043) and the processing composition includes an oximated polydiacetone acrylamide thickening agent (as described in U.S. Pat. No. 4,202,694). In another preferred embodiment a compound of the invention is incorporated in the photosensitive element in a layer between the substrate and the silver halide emulsion closest to the substrate. In this manner there is a delay in the cleavage of the compound and/or the diffusion of the substituted phenylmercaptoazole moiety through the film unit.

The advantageous results obtained through the use of the phenylmercaptoazole compounds in diffusion transfer film units are not completely understood. However, to further aid those skilled in the art to understand and practice the invention, the proposed theoretical mechanism by which the advantageous results are thought to be effected will be discussed here. It should be understood, however, that the results provided by these compounds in diffusion transfer photographic systems have been observed from extensive experimentation and the proposed theoretical mechanism is not be be construed as limiting of the invention. It is theorized that the results obtained according to the invention are due to the compounds performing different functions at different stages of the development process, that is, as weak silver solvents and promoters of development a one stage of the development process and as development inhibitors, or restrainers, at another stage of the development process, and that the dual functions of these compounds within the diffusion transfer photographic system are pH dependent.

It is well known that in the diffusion transfer photographic development process the pH of any particular location within the film unit varies with time. Typically, the processing composition employed in the process has a very high pH, e.g., from about 13–14, and during the development process each layer of the multilayer film unit goes through a broad pH range which includes very high pH levels and relatively low pH levels. When the pH is above the pKa of the oxime substituent on the phenyl ring, the dianion is formed, for example,

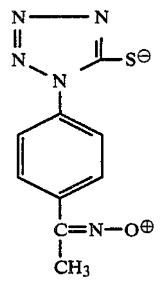

and acts as a weak silver solvent to form relatively soluble silver salts, thus promoting development. When the pH falls below the pKa of the oxime substituent the monoanion is formed, for example,

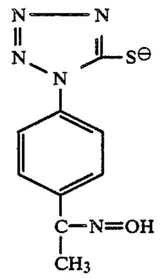

and the silver salt of the monoanion of the compound is very low in solubility resulting in a development restrainer action.

In view of the foregoing discussion, it will be understood that, according to one embodiment of the invention, development of the exposed diffusion transfer photosensitive element is carried out with a processing composition having an initial pH substantially equal to or above the pKa of the oxime substituent, at least for some period of time, when the processing composition comes into contact with the mercaptoazole compound so as to enable the substituent to ionize to form the dianion. In addition, at some point during the development process the pH of the environment where the compound is located is reduced below the pKa of the oxime substituent so as to form the monoanion.

The pKa of the oxime substituent in compound I is 11.4±0.1. Solubility product measurements were made for the silver salt of phenylmercaptotetrazole (PMT) at pH 13.5 and for the silver salt of compound I at pH 7 and pH 13.5 (above and below the pKa of the oxime substituent). The results are listed in Table I.

TABLE I

| COMPOUND | pH | Ksp |
|---|---|---|
| PMT | 7 | $3 \times 10^{-16}$* |
| | 13.5 | $4 \times 10^{-16}$ |
| I | 7 | $\sim 1 \times 10^{-16}$ |
| | 13.5 | $2 \times 10^{-15}$ |

It is seen that while phenylmercaptotetrazole was relatively unaffected by pH the ionization of the oxime substituent increased the solubility of the silver salt of compound I by an order of magnitude.

The solubilities of the silver salts of PMT and compound I in the presence of excess amounts of their anions also were measured at pH 7.0 and 13.5. Each solution was $4 \times 10^{-3}$ molar in silver. The results are shown in Table II wherein the solubility data is expressed in μmoles/liter of total silver.

TABLE II

| | COMPOUND I | | PMT | |
|---|---|---|---|---|
| Molar Ratio | pH | | pH | |
| Ligand/Ag | 7.0 | 13.5 | 7.0 | 13.5 |
| 1.25/1 | <1 | 19 | <1 | 1 |
| 1.75/1 | <1 | 44 | <1 | 2 |
| 2.13/1 | <1 | 93 | 1 | 4 |
| 2.5/1 | 2 | 140 | 3 | 8 |
| 4.5/1 | 2 | 320 | 15 | 18 |
| 7.5/1 | 5 | 1400 | 58 | 63 |

It can be seen that compound I is a weak to moderate silver solvent at high pH while PMT is not. Further, it is evident that when the oxime substituent is protonated it reverts to behaviour which is similar to that of PMT. In fact, compound I forms an even less soluble silver salt in neutral solution than does PMT, thus giving it a sharper effect on the availability of silver in soluble form as the pH drops in the diffusion transfer development process.

The compounds of the invention are useful generally in any photographic system where a development restrainer or development restrainer precursor is desirable. Thus the compounds may be incorporated in a conventional photographic element which is developed by processing with an aqueous alkaline processing composition having a pH below the pKa of the compound.

The invention will now be described further in detail with respect to specific preferred embodiments by way of examples, it being understood that these are illustrative only and the invention is not intended to be limited to the materials, conditions, process parameters, etc. which are recited therein. All parts and percentages are by weight unless otherwise indicated.

EXAMPLE I

A solution of 27.0 g (0.2 m) of 4'-aminoacetophenone and 24.4 g (0.2 m) of 4'N,N-dimethylaminopyridine in 500 ml of dry tetrahydrofuran in a liter round-bottom flask was swept with dry nitrogen while being stirred and 13.0 ml (0.2 m) of carbon disulfide were added. The flask was stoppered tightly and the solution stirred at ambient temperature for 48 hours. The yellow precipitate which formed was collected, washed with dry tetrahydrofuran and dried at ambient temperature under reduced pressure for about 1 to 3 hours to give 33.2 g (0.1 m, 50% yield) of the dithiocarbamate salt.

A solution of the 33.2 g of dithiocarbamate salt in 300 ml of dry tetrahydrofuran in a liter round-bottom flask was cooled in an icebath and to it there was added over a period of about 15 minutes under an atmosphere of dry nitrogen with stirring, a solution of 10.2 ml (0.107 m) of ethyl chloroformate in 50 ml of tetrahydrofuran. The gas inlet of the flask was connected to an aqueous alkali trap by means of a tube of anhydrous calcium sulfate and the mixture stirred at the icebath temperature for 15 minutes followed by stirring at ambient temperature for 18 hours. The filtrate was recovered by vacuum filtration and evaporated to give a light yellow solid.

The solid was thoroughly dispersed in 500 ml of toluene and the mixture filtered under vacuum. The filtrate was evaporated and dried at ambient temperature under reduced pressure to give 15.5 g (44% yield) of p-acetylphenylisothiocyanate, m.p. 72°-5° C. as light yellow crystals.

A solution of 18.5 g (0.104 m) of p-acetylphenylisothiocyanate in 174 ml of chloroform was mixed with a solution of 41.8 g (0.64 m) of sodium azide in 174 ml of distilled water and the mixture stirred vigorously while being heated at reflux under nitrogen for five hours. After cooling to ambient temperature the phases were separated and the aqueous phase collected and acidified to a pH of about 3 with concentrated hydrochloric acid. The yellow precipitate was collected by vacuum filtration, washed thoroughly six times with 200 ml of water and dried at ambient temperature under reduced pressure to give 20.15 g (88% yield) of a compound having the formula

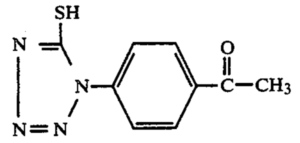

m.p. 170°-2° C. (dec). In ethanol solution the compound exhibited $\lambda_{max}$235 nm ($\epsilon$=16,800), 251 nm ($\epsilon$=18,400) and 326 nm ($\epsilon$=5,640).

An ice cold mixture of 20.15 g of the above compound and 6.72 g of hydroxylamine hydrochloride in 490 ml of water was formed and to it there was added with stirring 15.67 g of sodium acetate (portionwise) followed by 1.35 g of sodium bicarbonate (portionwise, to control foaming). The mixture was stirred under nitrogen at ambient temperature for 18 hours and then acidified to about pH 3 with concentrated hydrochloric acid. The light yellow solid which formed was collected by vacuum filtration, washed thoroughly six times with 200 ml volumes of water and then dried under reduced pressure at ambient temperature to give 20.69 g (96% yield of compound I, m.p. 184°-5° C. (dec). In ethanol solution the compound exhibited $\lambda_{max}$=235 nm ($\epsilon$=15,6000), 257 nm ($\epsilon$=16,600) and 299 nm ($\epsilon$=7,000).

EXAMPLE II

As a control a film unit was prepared as follows: The photosensitive element comprised a subcoated transparent polyethylene terephthalate photographic film base having coated thereon the following layers is succession:

1. a layer of sodium cellulose sulfate coated at a coverage of about 27.6 mgs/m$^2$;

2. a layer of a cyan dye developer represented by the formula

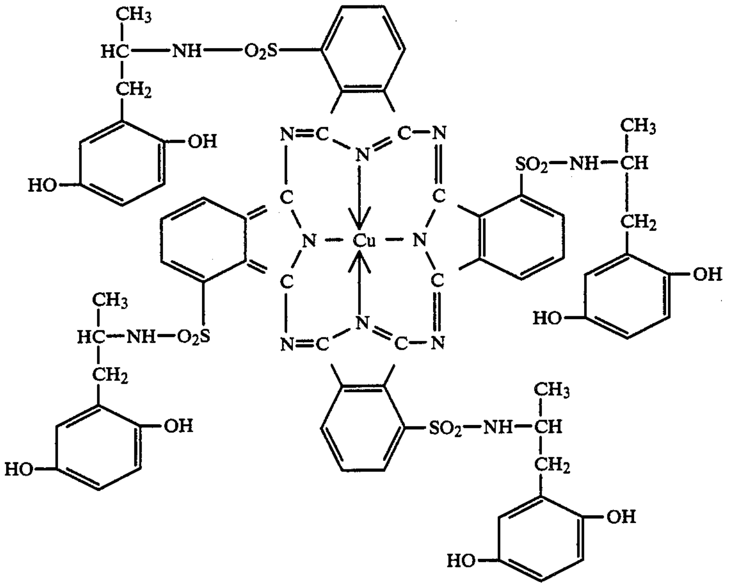

dispersed in gelatin and coated at a coverage of about 747 mgs/m$^2$ of the dye developer and about 1554 mgs/m$^2$ of gelatin and including about 68 mgs/m$^2$ of 4'-methylphenylhydroquinone and about 270 mgs/m$^2$ of 2-phenylbenzimidazole;

3. a red-sensitive silver iodobromide emulsion layer coated at a coverage of about 1280 $mgs/m^2$ of silver and about 768 $mgs/m^2$ of gelatin;

4. an interlayer comprising about 2505 $mgs/m^2$ of a 60-29-6-4-0.4 pentapolymer of butylacrylate, diacetone acrylamide, methacrylic acid, styrene and acrylic acid and about 78 $mgs/m^2$ of polyacrylamide;

5. A layer of a magenta dye developer represented by the formula

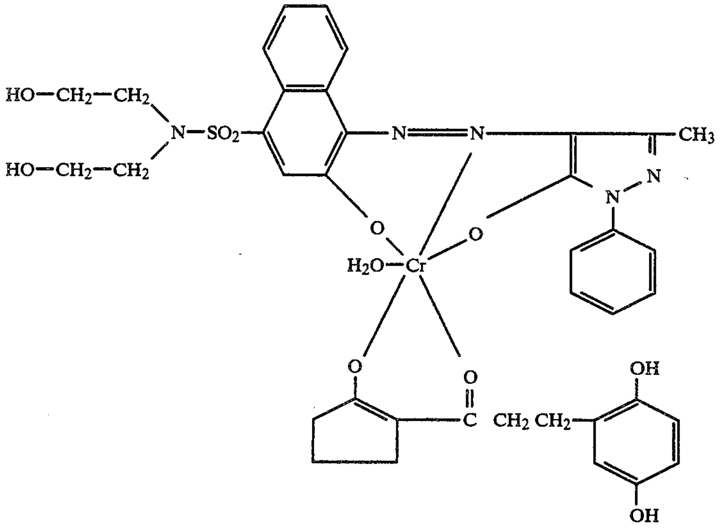

dispersed in gelatin and coated at a coverage of about 646 $mgs/m^2$ of the dye developer, about 448 $mgs/m^2$ of gelatin and including about 229 $mgs/m^2$ of 2-phenylbenzimidazole;

6. a green-sensitive silver iodobromide emulsion layer coated at a coverage of about 1050 $mgs/m^2$ of silver and about 504 $mgs/m^2$ of gelatin;

7. a layer comprising about 215 $mgs/m^2$ of dodecylamino reductone and about 215 $mgs/m^2$ of gelatin;

8. an interlayer comprising about 1366 $mgs/m^2$ of the pentapolymer described in layer 4, about 87 $mgs/m^2$ of polyacrylamide and about 71 $mgs/m^2$ of succindialdehyde;

9. a layer of a yellow dye developer represented by the formula

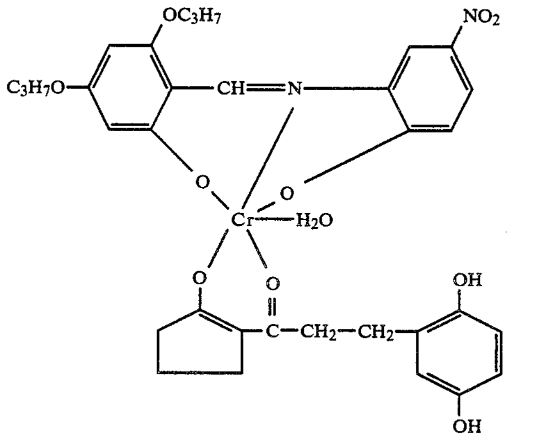

dispersed in gelatin and coated at a coverage of about 968 $mgs/m^2$ of dye developer and about 451 $mgs/m^2$ of gelatin and including about 208 $mgs/m^2$ of 2-phenylbenzimidazole;

10. a blue-sensitive silver iodobromide emulsion layer coated at a coverage of about 1280 $mgs/m^2$ of silver, about 775 $mgs/m^2$ of gelatin and about 306 $mgs/m^2$ of 4-methyl phenyl hydroquinone;

11. an overcoat layer coated at a coverage of about 461 $mgs/m^2$ of gelatin and about 21 $mgs/m^2$ of carbon black.

The image-receiving element comprised a transparent polyethylene terephthalate film base coated with the following layers is succession:

1. as a polymeric acid layer approximately 9 parts of a ½ butyl ester of polyethylene/maleic anhydride copolymer and 1 part of polyvinyl butyral coated at a coverage of about 2450 $mgs/ft^2$ (26,372 $mgs/m^2$);

2. a timing layer containing about 425 $mgs/ft^2$ (4575 $mgs/m^2$) of a 60-30-4-6 tetrapolymer of butylacrylate, diacetone acrylamide, styrene and methacrylic acid and including 9% polyvinyl alcohol; and 3. a polymeric image receiving layer of: (a) 3 parts of a mixture of 2 parts polyvinyl alcohol and 1 part poly-4-vinyl pyridine and (b) 1 part of a graft copolymer comprised of 4-vinylpyridine (4VP) and vinylbenzyl trimethyl ammonium chloride (TMQ) grafted onto hydroxyethyl cellulose (HEC) at a ratio of HEC/4VP/TMQ of 2.2/2.2/1 coated at a coverage of about 300 $mgs/ft^2$ (3229 $mgs/m^2$).

The film unit was processed with an aqueous alkaline processing composition as follows:

| | |
|---|---|
| Titanium dioxide | 38.05 g. |
| Carboxymethyl hydroxyethyl cellulose | 2.00 g. |
| Potassium hydroxide (45% aqueous solution) | 11.11 g. |
| Benzotriazole | 0.28 g. |
| 6-methyl uracil | 0.30 g. |
| N—hydroxyethyl-N,N',N'—tris-carboxymethyl ethylene diamine | 0.75 g. |
| Polyethylene glycol (MW 4000) | 0.45 g. |
| Bis(2-aminoethyl)sulfide | 0.02 g. |
| Colloidal silica (30% aqueous dispersion) | 1.85 g. |
| N—phenethyl-α-picolinium bromide (50% aqueous solution) | 2.55 g. |
| 4-aminopyrazolo(3,4-d)pyrimidine | 0.25 g. |
| | 0.30 g. |

-continued

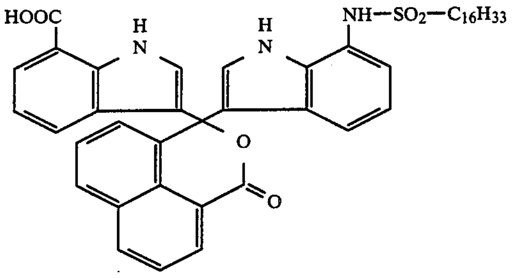

1.36 g.

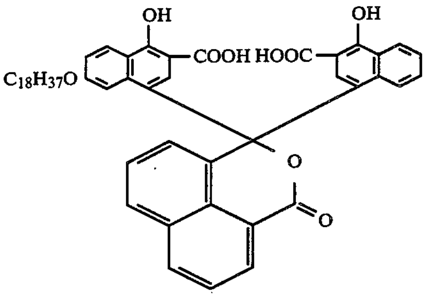

Water to make a total of 100. g.

A film unit according to the invention was prepared identical to the control with the exception that the processing compostion further included 0.05% of compound I.

The film units were processed at room temperature as follows: one half of each film unit was exposed through the transparent base of the image-receiving element to light from a Xenon source (100 meter-candle-seconds) which was passed in turn through an ultraviolet filter, neutral density filters to reduce the film plane light flux to 0.5 mcs and a Wratten 47B blue filter; the other half of each film unit was not exposed. The film units were then processed by passing them through a pair of rollers at a gap spacing of 0.0030" and the relative amount of silver developed (a function of the infra-red light absorbed) was measured as a function of time for both the exposed and unexposed areas. The relative amount of developed silver vs time curves are shown in FIG. 1. It is seen that the presence of compound I reduced fog development (relative amount of developed silver in unexposed areas) in comparison to the control. It is also apparent that the difference between the relative amount of silver developed in exposed and unexposed regions in the presence of compound I is significantly greater than the corresponding difference for the control.

Figure 2:
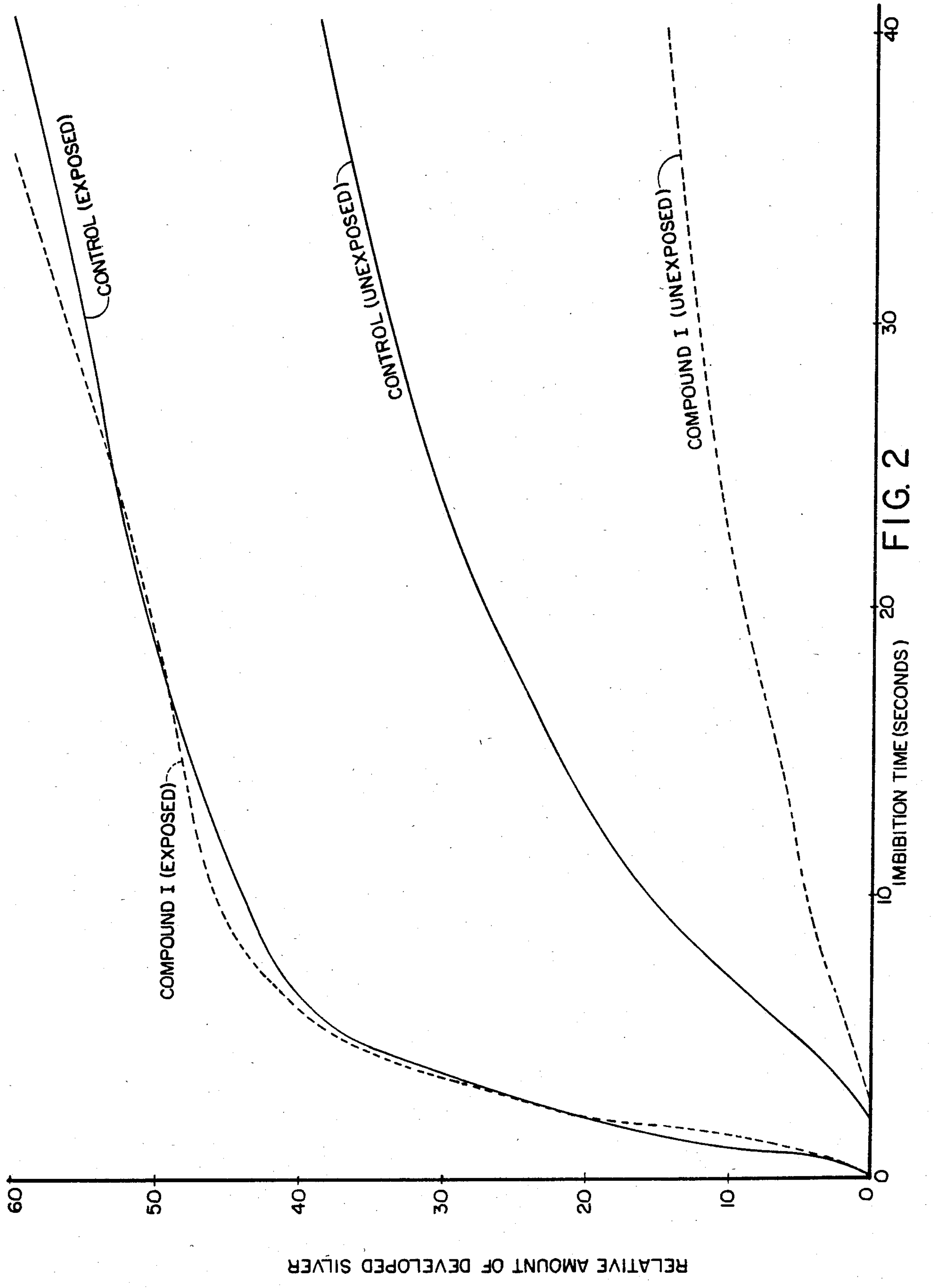
FIG. 2 is a similar graphical illustration for the same film units processed at 95° F.

The experiment was repeated with processing being carried out at 95° F. The relative amount of developed silver vs time curves are shown in FIG. 2. It is seen that fog development in the control increased significantly at the higher processing temperature, whereas the increase was only slight with compound I present. Further, at the higher processing temperature the presence of compound I greatly reduced fog development in comparison to the control without any appreciable change in the rate at which the silver density was developed in the exposed areas.

EXAMPLE III

As a control a film unit was prepared as follows: The photosensitive element comprised a subcoated opaque polyethylene terephthalate photographic film base having coated thereon the following layers in succession:

1. a cyan dye developer layer coated at a coverage of about 742 $mgs/m^2$ of the cyan dye developer described in Example II, about 1485 $mgs/m^2$ of gelatin, about 67 $mgs/m^2$ of 4'-methylphenylhydroquinone and about 270 $mgs/m^2$ of 2-phenylbenzimidazole;
2. a red sensitive silver iodobromide emulsion layer coated at a coverage of about 1290 $mgs/m^2$ of silver and about 775 $mgs/m^2$ of gelatin;
3. an interlayer of a 60-30-4-6 tetrapolymer of butyl acrylate, diacetone acrylamide, styrene and methacrylic acid coated at a coverage of about 2582 $mgs/m^2$ of the tetrapolymer and about 68 $mgs/m^2$ of polyacrylamide;
4. a magenta dye developer layer coated at a coverage of about 646 $mgs/m^2$ of the magenta dye developer described in Example II, about 452 $mgs/m^2$ of gelatin, about 11 $mgs/m^2$ of carbon black and about 226 $mgs/m^2$ of 2-phenylbenzimidazole;
5. a green sensitive silver iodobromide layer coated at a coverage of about 795 $mgs/m^2$ of silver and about 525 $mgs/m^2$ of gelatin;
6. an interlayer including about 1452 $mgs/m^2$ of the tetrapolymer described in layer 3, about 75 $mgs/m^2$ of polyacrylamide and about 71 $mgs/m^2$ of succindialdehyde;
7. a yellow dye developer layer coated at a coverage of about 968 $mgs/m^2$ of the yellow dye developer described in Example II, about 452 $mgs/m^2$ of gelatin, about 27 $mgs/m^2$ of carbon black and about 204 $mgs/m^2$ of 2-phenylbenzimidazole;
8. a blue sensitive silver iodobromide emulsion layer coated at a coverage of about 1280 $mgs/m^2$ of silver, about 563 $mgs/m^2$ of gelatin and about 204 $mgs/m^2$ of 4'-methyl phenyl hydroquinone;
9. an overcoat layer coated at a coverage of about 484 $mgs/m^2$ of gelatin and about 43 $mgs/m^2$ of carbon black.

The image-receiving element was identical to that described in Example II.

The film unit was processed with an aqueous alkaline processing composition which was the same as that described in Example II with the exception that it included 0.55 g of benzotriazole and did not include any 4-aminopyrazolo(3,4-d) pyrimidine.

The film unit was then exposed at 75° F. (0.5 meter-candle-seconds) on a sensitometer to a photographic test exposure scale, or step wedge, through the transparent support of the image receiving element and processed with the processing composition by passing the film unit through a pair of pressure rollers set at a gap spacing of about 0.0030 inch. The film unit was retained intact and viewed through the transparent base. There was obtained a well developed multicolor image.

The neutral density column of the image was read on the densitometer to obtain the $D_{max}$ values for red, green and blue, respectively. In addition, the speed of the red, green and blue curves, respectively (defined as the negative log of the relative exposure required to give red, green and blue absorption in the neutral column a reflection density of 0.75) was measured. The values obtained are shown in Table III.

The experiment was repeated with six additional film units (IIIA-IIIF) with the exception that the processing composition further included compound I in the amounts shown in Table III.

In addition, the control and certain of the other film units were processed at 95° F.

TABLE III

| Film | % Comp'd | 75° F. | | | | | |
|---|---|---|---|---|---|---|---|
| | | Dmax | | | Rel. Speed | | |
| Unit | I | R | G | B | R | G | B |
| Control | — | 2.31 | 2.20 | 2.22 | 1.41 | 1.29 | 1.23 |
| IIIA | 0.05 | 2.39 | 2.24 | 2.36 | 1.36 | 1.35 | 1.38 |
| IIIB | 0.06 | 2.43 | 2.28 | 2.38 | 1.39 | 1.40 | 1.44 |
| IIIC | 0.07 | 2.42 | 2.25 | 2.35 | 1.38 | 1.40 | 1.46 |
| IIID | 0.08 | 2.36 | 1.97 | 2.13 | 1.35 | 1.41 | 1.48 |
| IIIE | 0.09 | 2.35 | 1.91 | 2.04 | 1.40 | 1.48 | 1.55 |
| IIIF | 0.10 | 2.32 | 1.81 | 1.88 | 1.40 | 1.52 | 1.60 |
| | | 95° F. | | | | | |
| Film | | Dmax | | | Rel. Speed | | |
| Unit | | R | G | B | R | G | B |
| Control | | −0.45 | −0.28 | −0.45 | +0.10 | +0.16 | +0.08 |
| IIIA | 0.05 | — | — | — | — | — | — |
| IIIB | 0.06 | −0.20 | −0.05 | −0.12 | +0.05 | +0.01 | −0.08 |
| IIIC | 0.07 | −0.17 | −0.02 | −0.10 | +0.04 | +0.01 | −0.08 |
| IIID | 0.08 | −0.13 | +0.26 | +0.12 | +0.07 | +0.02 | −0.06 |
| IIIE | 0.09 | −0.07 | +0.33 | +0.23 | +0.02 | −0.04 | −0.10 |
| IIIF | 0.10 | — | — | — | — | — | — |

The results show that at room temperature processing (75° F.) the presence of compound I provided an increase in the $D_{max}$ of the individual colors to concentrations up to 0.07% and an increase in the green and blue speeds in each film unit. When the film units were processed at 95° F. the presence of compound I provided a significant improvement over the control in $D_{max}$ since the $D_{max}$ of the individual colors went down considerably less, in comparison to the values obtained at 75° F., in most instances and actually increased in others.

EXAMPLE IV

A mixture of compound I (11.647 g, 49.58 mmol), β-bromopropionitrile (6.626 g, 49.58 mmol) and sodium bicarbonate (4.17 g, 49.58 mmol) in 200 ml of dry acetonitrile was magnetically stirred overnight in a 55° C. bath under nitrogen. The reaction mixture was vacuum filtered and the filtrate was stripped of solvent by rotary evaporation giving an orange oily residue. The residue was taken up in ethyl acetate (75 ml) and to the solution there were added seed crystals and 150 ml of hexane. The mixture was scratched and stored overnight in a refrigerator. The crystals which formed were collected by filtration, washed twice with hexane and dried to give 12.74 g of compound II as light yellow crystals, m.p. 111°-113° C. The structure of the product was confirmed by IR, UV and NMR spectra and thin layer chromatography.

EXAMPLE V

A set of film units (VA), identical to those described in Example III except that the processing composition contained 0.05% of compound I were processed at 75° F. and 95° F. The data for the control film unit of Example III were used for comparison.

TABLE IV

| Film | 75° F. | | | | | |
|---|---|---|---|---|---|---|
| | Dmax | | | Rel. Speed | | |
| Unit | R | G | B | R | G | B |
| Control | 2.31 | 2.20 | 2.22 | 1.41 | 1.29 | 1.23 |
| VA | 2.27 | 2.22 | 2.26 | 1.39 | 1.39 | 1.42 |
| | 95° F. | | | | | |
| | Δ Dmax | | | Δ Rel. Speed | | |
| | R | G | B | R | G | B |
| Control | −0.45 | −0.28 | −0.45 | +0.10 | +0.16 | +0.08 |
| VA | −0.15 | −0.01 | +0.02 | −0.08 | +0.05 | −0.04 |

It can be seen that again the presence of compound I provided significant increases in the green and blue relative speeds at 75° F. and provided significant improvement in the red, green and blue $D_{max}$ at 95° F. with the relative speeds of these colors being desirably closer than in the control.

EXAMPLE VI

This experiment represents a comparison of compound I and phenylmercaptotetrazole (PMT) with a control at room temperature.

The control film unit comprised a subcoated opaque film base having the following layers coated thereon in succession:

1. a layer of sodium cellulose sulfate coated at a coverage of about 100 $mgs/m^2$;
2. a cyan dye developer layer coated at a coverage of about 635 $mgs/m^2$ of the cyan dye developer described in Example II, about 430 $mgs/m^2$ of gelatin; about 237 $mgs/m^2$ of N-dodecylaminopurine and about 128 $mgs/m^2$ of 4'-methyl phenyl hydroquinone;
3. a red-sensitive silver iodobromide emulsion layer coated at a coverge of about 1500 $mgs/m^2$ of silver and about 900 $mgs/m^2$ of gelatin;
4. an interlayer comprising about 1264 $mgs/m^2$ of the pentapolymer described in Example II and about 67 $mgs/m^2$ of polyacrylamide;
5. a magenta dye developer layer coated at a coverage of about 646 $mgs/m^2$ of a magenta dye developer represented by the formula

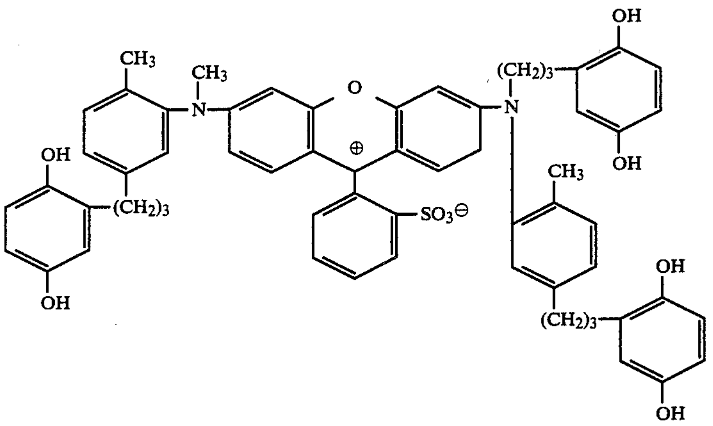

and about 323 $mgs/m^2$ of gelatin;

6. a green-sensitive silver iodobromide emulsion layer coated at a coverage of about 1300 $mgs/m^2$ of silver and about 596 $mgs/m^2$ of gelatin;

7. an interlayer comprising about 950 $mgs/m^2$ of the pentapolymer described in Example II and about 50 $mgs/m^2$ of polyacrylamide;

8. a yellow dye developer layer coated at a coverage of about 820 $mgs/m^2$ of the yellow dye developer described in Example II and about 328 $mgs/m^2$ of gelatin;

9. a spacer layer comprising about 150 $mgs/m^2$ of N-dodecylaminopurine and about 150 $mgs/m^2$ of gelatin;

10. a blue sensitive silver iodobromide emulsion layer coated at a coverage of about 1200 $mgs/m^2$ of silver, about 421 $mgs/m^2$ of gelatin and about 320 $mgs/m^2$ of 4' methyl phenyl hydroquinone; and 11. a topcoat layer comprising about 484 $mgs/m^2$ of gelatin.

The image-receiving element comprised a transparent base having coated thereon in succession:

1. a polymeric acid layer as described in Example V.

2. a timing layer comprising about 2570 $mgs/m^2$ of the pentapolymer described in Example II and about 205 $mgs/m^2$ of polyacrylamide;

3. a polymeric image receiving layer coated at a coverage of about 2990 $mgs/m^2$ of: (a) 3 parts of a mixture of 2 parts polyvinyl alcohol and 1 part poly-4-vinylpyridine and (b) 1 part of a graft copolymer comprised of 4-vinylpyridine (4VP) and vinyl benzyl trimethyl ammonium chloride (TMQ) grafted onto hydroxyethylcellulose (HEC) at a ratio HEC/4VP/TMQ of 2.2/2.2/1; and about 103 $mgs/m^2$ of 1,4-butanediol diglycidyl ether;

4. a topcoat layer comprising about 721 $mgs/m^2$ of a polyoxyethylene-polyoxypropylene block copolymer (Pluronic F-127), commercially available from BASF Wyandotte Co.) and about 309 $mgs/m^2$ of polyvinylalcohol.

The control film unit was processed with a processing composition as described in Example II as a control with the exception that it included 0.55 g of benzotriazole and 0.93 g of the aqueous colloidal silica dispersion.

Two additional film units (VIA and VIB) were prepared and processed in the same manner with the exception that the processing composition further included 0.05% of PMT and compound I respectively. The results are shown in Table V.

TABLE V

| Film | Dmax | | | Dmin | | | Rel. Speed | | |
|---|---|---|---|---|---|---|---|---|---|
| Unit | R | G | B | R | G | B | R | G | B |
| Control | 1.80 | 2.24 | 1.65 | 0.21 | 0.21 | 0.18 | 1.41 | 1.37 | 1.64 |
| VI A | 1.75 | 2.23 | 2.20 | 0.23 | 0.25 | 0.76 | 1.29 | 1.03 | * |
| VI B | 1.81 | 2.27 | 2.06 | 0.23 | 0.22 | 0.19 | 1.34 | 1.33 | 1.27 |

*blue relative speed too slow to measure

It is seen that the presence of PMT caused a large increase in the blue $D_{min}$ and a very large decrease in the blue speed, thus indicating that the PMT restrained development of the blue sensitive silver halide emulsion prematurely. The presence of compound I provided an increase in the blue $D_{max}$ without any increase in the blue $D_{min}$.

EXAMPLE VII

As a control a film unit was prepared as follows: the photosensitive element comprised a subcoated transparent polyethylene terephthalate photographic film base having coated thereon the following layers in succession:

1. a layer of sodium cellulose sulfate coated at a coverage of about 14.4 $mgs/m^2$;

2. a cyan dye developer layer comprising about 747 $mgs/m^2$ of the cyan dye developer illustrated in Example II, about 1554 $mgs/m^2$ of gelatin, about 270 $mgs/m^2$ of 2-phenylbenzimidazole and about 68 $mgs/m^2$ of 4'-methylphenylhydroquinone;

3. a red-sensitive silver iodobromide emulsion layer coated at a coverage of about 1280 $mgs/m^2$ of silver and about 768 $mgs/m^2$ of gelatin;

4. an interlayer comprising about 2505 $mgs/m^2$ of the pentapolymer described in Example II and about 78 $mgs/m^2$ of polyacrylamide;

5. a magenta dye developer layer comprsing about 646 $mgs/m^2$ of the magenta dye developer described in Example II, about 452 $mgs/m^2$ of gelatin and about 229 $mgs/m^2$ of 2-phenylbenzimidazole;

6. a green-sensitive silver iodobromide emulsion layer coated at a coverage of about 510 $mgs/m^2$ of silver and about 224 $mgs/m^2$ of gelatin;

7. a spacer layer comprising about 1045 $mgs/m^2$ of polymethylmethacrylate and about 55 $mgs/m^2$ of polyacrylamide;

8. a green-sensitive silver iodobromide emulsion layer coated at a coverage of about 700 $mgs/m^2$ of silver and about 336 $mgs/m^2$ of gelatin;

9. an interlayer comprising about 1366 $mgs/m^2$ of the pentapolymer described in Example II and about 87 $mgs/m^2$ of polyacrylamide;

10. a yellow dye developer layer comprising about 820 $mgs/m^2$ of the yellow dye developer illustrated in Example II, about 384 $mgs/m^2$ of gelatin and about 208 $mgs/m^2$ of 2-phenylbenzimidazole;

11. a blue-sensitive silver iodobromide emulsion layer coated at a coverage of about 1280 $mgs/m^2$ of silver, about 775 $mgs/m^2$ of gelatin and about 306 $mgs/m^2$ of 4'-methylphenylhydroquinone;

12. a top coat layer of about 484 $mgs/m^2$ of gelatin.

The image-receiving element comprised a transparent subcoated polyethylene terephthalate film base on which the following layers were coated in succession:

1. as a polymeric acid layer approximately 9 parts of a ½ butyl ester of polyethylene/maleic anhydride copolymer and 1 part of polyvinyl butyral coated at a coverage of about 26,372 $mgs/m^2$;

2. a timing layer coated at a coverage of about 10,000 $mgs/m^2$ of a graft tetrapolymer of diacetone acrylamide, acrylamide, β-cyanoethylacrylate and 2-acrylamido-2-methane sulfonic acid on polyvinylalcohol;

3. a polymeric image receiving layer coated at a coverage of about 2200 $mgs/m^2$ of: (a) 3 parts of a mixture of 2 parts polyvinyl alcohol and 1 part poly-4-vinylpyridine and (b) 1 part of a graft copolymer comprised of 4-vinylpyridine (4VP) and vinyl benzyltrimethyl ammonium chloride (TMQ) grafted onto hydroxyethyl cellulose (HEC) at a ratio HEC/4VP/TMQ of 2.2/2.2/1; and about 74 $mgs/m^2$ of 1,4-butanediol diglycidyl ether;

4. a top coat layer comprising about 320 $mgs/m^2$ of polyvinyl alcohol.

The film unit was processed with a processing composition as described in Example VI.

Three additional film units were prepared (VIIA-VIIC). Film units VIIA-VIIC further included 1 $mg/m^2$, 2 $mgs/m^2$ and 3 $mgs/m^2$, respectively, of compound I in layer 5 of the photosensitive element. An identical set of film units was also processed at 95° F. The results are shown in Table VI.

TABLE VI

75° F.

| Film Unit | Dmax R | Dmax G | Dmax B | Rel. Speed R | Rel. Speed G | Rel. Speed B |
|---|---|---|---|---|---|---|
| Control | 1.95 | 1.67 | 2.23 | 1.50 | 1.49 | 1.32 |
| VII A | 2.03 | 1.75 | 2.25 | 1.52 | 1.46 | 1.33 |
| VII B | 2.09 | 1.70 | 2.24 | 1.47 | 1.46 | 1.33 |
| VII C | 2.14 | 1.78 | 2.28 | 1.41 | 1.39 | 1.29 |

95° F.

| | Δ Dmax R | Δ Dmax G | Δ Dmax B |
|---|---|---|---|
| Control | −0.56 | −0.20 | −0.18 |
| VII A | −0.48 | −0.19 | −0.15 |
| VII B | −0.27 | −0.09 | −0.11 |
| VII C | −0.22 | −0.06 | −0.11 |

It can be seen that at room temperature the presence of compound I provided an increase in red and green $D_{max}$. At 95° F. processing the presence of compound I gave smaller losses (varying with the coverages) of red, blue and green $D_{max}$.

EXAMPLE VIII

As a control a film unit was prepared as follows: the negative element comprised an opaque subcoated polyethylene terephthalate film base on which the following layers were coated in succession.

1. as a polymeric acid layer approximately 9 parts of a ½ butyl ester of polyethylene/maleic anhydride copolymer and 1 part of polyvinyl butyral coated at a coverage of about 26,460 $mgs./m.^2$;

2. a timing layer comprising about 97% of a 60-29-6-4-0.4 pentapolymer of butylacrylate, diacetone acrylamide, methacrylic acid, styrene and acrylic acid and about 3% polyvinylalcohol coated at a coverage of about 3000 $mgs./m.^2$;

3. a cyan dye developer layer comprising about 511 $mgs./m.^2$ of the cyan dye developer described in Example II, about 70 $mgs./m.^2$ of 4'methyl phenyl hydroquinone and about 317 $mgs./m.^2$ of gelatin;

4. a red-sensitive silver iodobromide emulsion layer comprising about 1378 $mgs./m.^2$ of silver and about 827 $mgs./m.^2$ of gelatin;

5. an interlayer comprising about 2090 $mgs./m.^2$ of the pentapolymer described in layer 2, about 110 $mgs./m.^2$ of polyacrylamide and about 44 $mgs./m.^2$ of succinaldehyde;

6. a magenta dye developer layer comprising about 460 $mgs./m^2$ of a magenta dye developer represented by the formula

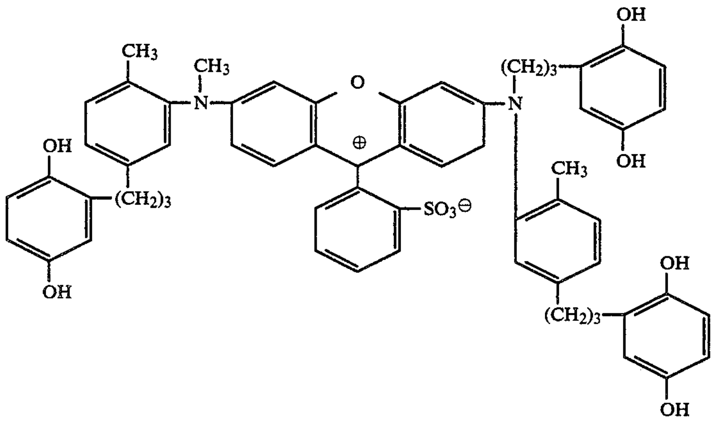

and about 210 $mgs./m.^2$ of gelatin;

7. a green-sensitive silver iodobromide emulsion layer comprising about 723 $mgs./m.^2$ of silver and about 318 $mgs./m.^2$ of gelatin;

8. an interlayer comprising about 1881 mgs./m.$^2$ of the pentapolymer described in layer 2 and about 99 mgs./m.$^2$ of polyacrylamide;

9. a yellow dye developer layer comprising about 689 mgs./m.$^2$ of the yellow dye developer described in Example I and about 276 mgs./m.$^2$ of gelatin;

10. a blue-sensitive silver iodobromide emulsion layer comprising about 764 mgs./m.$^2$ of silver, about 499 mgs./m.$^2$ of gelatin, and about 265 mgs./m.$^2$ of 4'-methyl phenyl hydroquinone; and 11. a topcoat layer of about 400 mgs./m.$^2$ of gelatin.

The image receiving element comprised a transparent subcoated polyethylene terephthalate film base upon which there was coated an image receiving layer coated at a coverage of about 300 mgs./ft.$^2$ (3229 mgs./m$^2$) of: (a) 3 parts of a mixture of 2 parts polyvinyl alcohol and 1 part poly-4-vinylpyridine and (b) 1 part of a graft copolymer comprised of 4-vinylpyridine (4VP) and vinyl benzyl trimethyl ammonium chloride (TMQ) grafted onto hydroxyethyl cellulose (HEC) at a ratio HEC/4VP/TMQ of 2.2/2.2/1; and about 5 mgs./ft.$^2$ (53.8 mgs./m.$^2$ of 1,4-butanediol diglycidyl ether.

The film unit was processed with a processing composition made up as follows:

| | |
|---|---|
| Water | 1632 ml. |
| $TiO_2$ | 2312.0 grams |
| Oximated polydiacetoneacrylamide | 32.0 grams |
| Potassium hydroxide (45% solution) | 468.0 grams |
| Benzotriazole | 22.0 grams |
| 4-aminopyrazole-(3,4-d)pyrimidine | 10.0 grams |
| 6-methyl uracil | 12.0 grams |
| N—hydroxyethyl-N,N'N'—triscarboxymethyl ethylene diamine | 30.0 grams |
| Polyethylene glycol (M.W. 4000) | 18.0 grams |
| Bis(2-aminoethyl)sulfide | 0.8 grams |
| Colloidal silica (30% solids) | 37.0 grams |
| N—phenethyl-α-picolinium bromide (50% solids) | 102.0 grams |
| Allopurinol | 3.3 grams |
| 2-methyl imidazole | 23.8 grams |
| 6-methyl-5-bromo azabenzimidazole | 4.8 grams |
| | 14.0 grams |
| 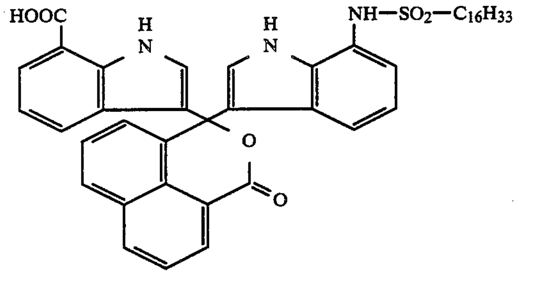 | |
| | 62.3 grams |
| 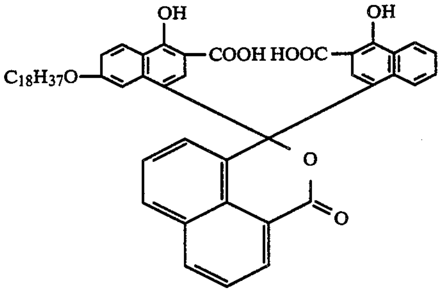 | |

The negative element was exposed (2 meter-candle-seconds) on a sensitometer to a test exposure scale with white light, and then brought together with the image receiving element and processed at room temperature (24° C.) by passing the film unit through a pair of rollers set at a gap spacing of about 0.0026 inch. The film unit was kept intact and viewed through the base of the image receiving element.

An identical film unit was processed in the same manner at 35° C. The neutral density columns of the images were read on a densitometer to obtain the Dmax and Dmin values for red, green and blue, respectively. The values obtained are shown in Table IX.

An additional film unit according to the invention (VIIIA) was prepared. This was identical to the control with the exception that the negative also included a top coat layer comprising about 20 mg/ft$^2$ (215 mgs/m$^2$) of blocked compound II according to the invention and about 20 mg/ft$^2$ of gelatin. The film units were processed as described above at 24° C. and at 35° C. The results are shown in Table VII.

TABLE VII

| | 24° C. | | | | | |
|---|---|---|---|---|---|---|
| Film | Dmax | | | Dmin | | |
| Unit | R | G | B | R | G | B |
| Control | 1.81 | 1.60 | 1.31 | 0.15 | 0.16 | 0.24 |
| VIIIA | 1.58 | 1.65 | 1.64 | 0.16 | 0.13 | 0.15 |
| | 35° C. | | | | | |
| Film | Dmax | | | Dmin | | |
| Unit | R | G | B | R | G | B |
| Control | 1.43 | 1.20 | 0.95 | 0.16 | 0.17 | 0.25 |
| VIIIA | 1.40 | 1.35 | 1.34 | 0.16 | 0.14 | 0.17 |

It can be seen that the presence of compound II provided significantly higher blue $D_{max}$ at 24° C. and 35° C. and slightly higher green $D_{max}$ at both temperatures.

EXAMPLE IX

A mixture of compound I (1.175 g, 5 mmol), sodium bicarbonate (420 mg. 5 mmol) and p-acetoxybenzyl chloride (925 mg, 5 mmol) in 30 ml of acetone was heated to boiling on a steam bath for 24 hours. The solution was vacuum filtered and the solvent was removed from the filtrate by rotary evaporation at 25° C. to give a light yellow oil. The oil was taken up in 30 ml of methanol, the solution vacuum filtered and the filtrate allowed to stand overnight in a refrigerator. The light yellow crystals which formed were collected by filtration and dried under reduced pressure at room temperature to give 1.34 g (70% yield) of compound III, m.p. 126°-127° C.

$C_{18}H_{17}N_5O_3S$ requires 56.38%C, 4.47%H, 18.27%N and 8.36%S. Elemental analysis found 56.50%C, 4.57%H, 18.27%N and 8.12%S.

Although the invention has been described with respect to specific preferred embodiments, it is not intended to be limited thereto but rather those skilled in the art will recognize that variations and modifications may be made therein which are within the spirit of the invention and the scope of the appended claims.

What is claimed is:

1. A compound which is represented by the formula

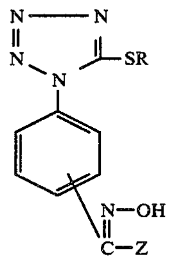

wherein R is H, an alkali metal or a group which is cleavable in aqueous alkaline medium and Z is H, alkyl having from 1 to 10 carbon atoms, benzyl, phenethyl or phenyl.

2. A compound as defined in claim 1 wherein Z is alkyl having from 1 to 10 carbon atoms.

3. A compound as defined in claim 2 wherein Z is $-CH_3$.

4. A compound as defined in claim 3 wherein R is H.

5. A compound as defined in claim 3 wherein R is a group which is cleavable in aqueous alkaline medium.

6. A compound as defined in claim 1 wherein R is H.

7. A compound as defined in claim 1 wherein R is a group which is cleavable in aqueous alkaline medium.

8. A compound as defined in claim 7 wherein R is $-CH_2-CH_2-SO_2-R_5$ wherein $R_5$ is alkyl.

* * * * *